United States Patent [19]

Wochnowski

[11] 4,300,201

[45] Nov. 10, 1981

[54] METHOD AND APPARATUS FOR ASCERTAINING THE BULK WEIGHT OF TOBACCO OR THE LIKE

[75] Inventor: Waldemar Wochnowski, Hamburg-Meiendorf, Fed. Rep. of Germany

[73] Assignee: Hauni-Werke Körber & Co. KG, Hamburg, Fed. Rep. of Germany

[21] Appl. No.: 76,411

[22] Filed: Sep. 17, 1979

[30] Foreign Application Priority Data

Sep. 23, 1978 [DE] Fed. Rep. of Germany ....... 2841494

[51] Int. Cl.³ .................. G01G 11/00; G06F 15/46
[52] U.S. Cl. .................................. 364/567; 131/108; 177/1; 177/25; 177/119
[58] Field of Search ............... 364/567, 568; 177/16, 177/25, 119, 1; 131/22 R, 21 R, 136

[56] References Cited

U.S. PATENT DOCUMENTS

| | | | |
|---|---|---|---|
| 3,254,728 | 6/1966 | Aquadro et al. | 364/567 X |
| 3,648,035 | 3/1972 | Hart et al. | 364/567 X |
| 3,875,383 | 4/1975 | Somerville et al. | 364/567 X |
| 3,959,636 | 5/1976 | Johnson et al. | 364/567 X |
| 3,979,055 | 9/1976 | Fathauer et al. | 364/567 X |
| 3,979,150 | 8/1976 | Wilson et al. | 364/567 X |
| 4,045,657 | 8/1977 | Falke | 364/567 X |
| 4,134,465 | 1/1979 | Takahama et al. | 364/567 X |
| 4,137,976 | 2/1979 | Grayson, Jr. | 364/567 X |

*Primary Examiner*—Edward J. Wise
*Attorney, Agent, or Firm*—Peter K. Kontler

[57] ABSTRACT

Bulk weight of a stream of tobacco leaves which are transported toward a destalking machine is ascertained by equalizing the stream and determining the density of the equalized stream. Signals which denote the density of the stream are used to regulate the rate of admission of compressed classifying air into the destalking machine wherein compressed air separates tobacco leaf laminae from tobacco ribs.

32 Claims, 5 Drawing Figures

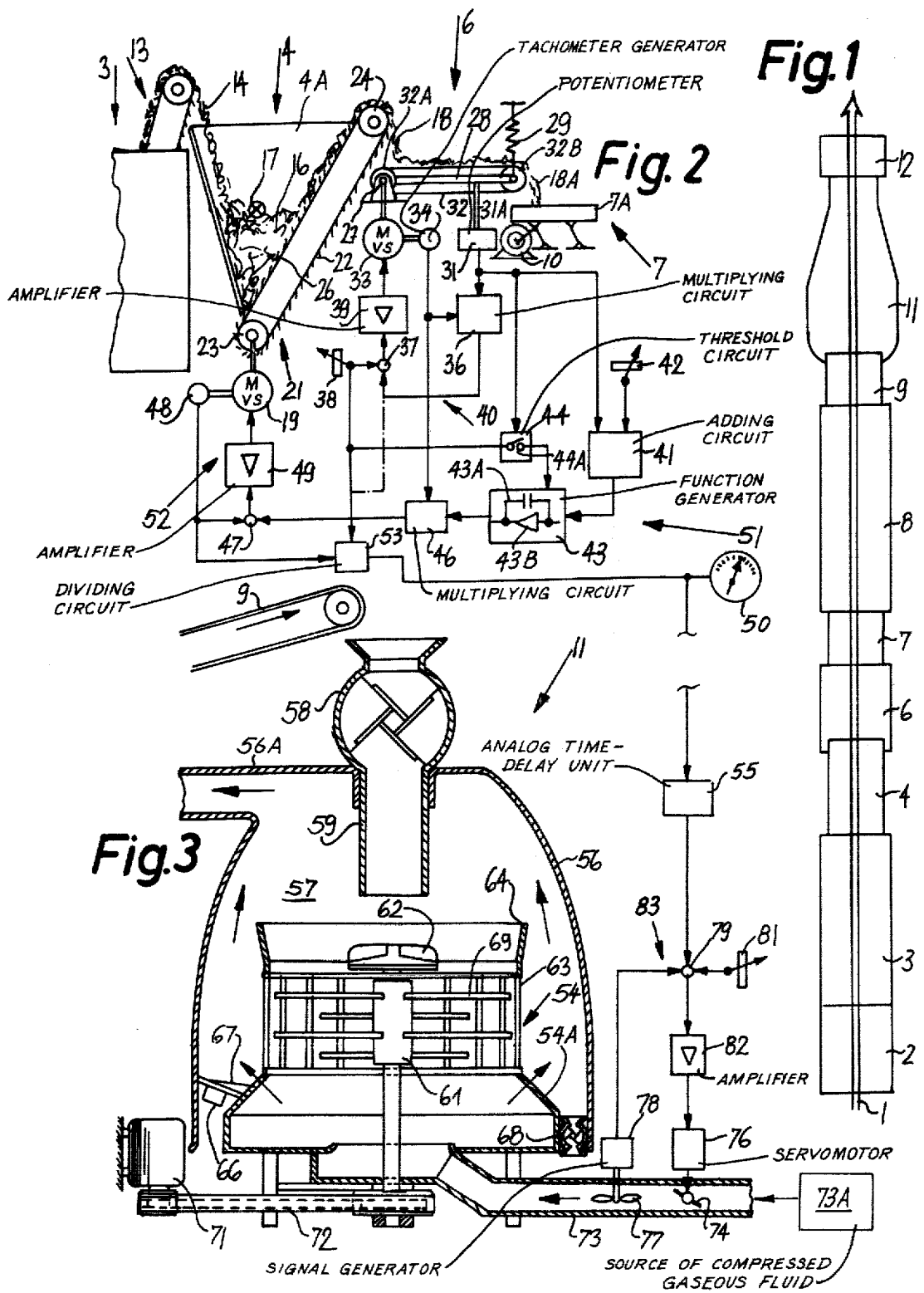

4,300,201

METHOD AND APPARATUS FOR ASCERTAINING THE BULK WEIGHT OF TOBACCO OR THE LIKE

CROSS-REFERENCE TO RELATED APPLICATION

The apparatus which is shown in FIGS. 1-3 of the present application is identical with the apparatus which is shown, described and claimed in the commonly owned copending application Ser. No. 76,208 filed Sept. 17, 1979 by Gerhard Graalmann et al for "Method and apparatus for forming an equalized tobacco stream".

BACKGROUND OF THE INVENTION

The present invention relates to a method and apparatus for ascertaining the bulk weight of tobacco or other particulate material which can be conveyed in the form of a continuous stream. More particularly, the invention relates to a method and apparatus for continuously ascertaining the bulk weight of a stream of particulate (granular, fibrous and/or sheet-like) material which moves lengthwise. Typical examples of materials which can be monitored in accordance with the present invention are various types and/or forms of tobacco including leaves, shreds, ribs, laminae and/or mixtures thereof.

It is often desirable to ascertain the specific weight and/or density of conveyed particulate material (for the sake of convenience, the material will be referred to as tobacco, with the understanding, however, that the method and apparatus can be practiced with equal or similar advantage in connection with the treatment of other types of granular, fibrous, sheet-like or analogous particulate materials). Furthermore, it is often desirable to ascertain variations in the density of tobacco; this enables the attendants in a processing plant (e.g., in a plant wherein tobacco leaves are subjected to primary treatment including shredding, changing the moisture content or the like) to reduce the likelihood of adversely affecting the quality of processed tobacco and/or eventual malfunctioning of the processing apparatus. At the present time, the fact that the density of tobacco has changed is recognized only upon detection of loss in quality of processed tobacco and/or as a result of detection of damage to a particular piece of equipment. Such belated determination that the density has changed is of little value.

OBJECTS AND SUMMARY OF THE INVENTION

An object of the invention is to provide a novel and improved method of automatically ascertaining the bulk weight of a continuously moving stream of tobacco or other particulate material.

Another object of the invention is to provide a method which renders it possible to continuously ascertain the density of particulate material which is conveyed in the form of an uninterrupted stream.

A further object of the invention is to provide a method which renders it possible to automatically regulate the treatment of an equalized stream of tobacco or other particulate material in dependency on changes in the bulk weight of material which forms the stream.

An additional object of the invention is to provide an apparatus which can be used to ascertain the bulk weight of a continuously moving stream of tobacco particles or the like.

Another object of the invention is to provide an apparatus which can be incorporated in existing production lines wherein particulate material, such as tobacco, is processed in large quantities and in a fully automatic way.

An additional object of the invention is to provide an apparatus which can equalize a continuous stream of tobacco so that the mass of successive unit lengths of the stream is constant or deviates only negligibly from a preselected optimum value.

Another object of the invention is to provide the apparatus with novel and improved means for regulating the rate of formation and transport of a continuous tobacco stream in a machine for the treatment of tobacco leaves or the like.

Another object of the invention is to provide the apparatus with novel and improved means for regulating the speed of various conveyors during transport of a continuous stream of tobacco leaves or the like.

One feature of the invention resides in the provision of a method of continuously ascertaining the bulk weight (normally measured in kilograms per cubic meter) of tobacco or other particulate material. The method comprises the steps of continuously conveying a stream of particulate material along a first and into and along a second portion of a predetermined path (such path can be defined by several conveyors including a first conveyor which draws particulate material from a source of supply and transports the resulting stream along the first portion of the path and a second conveyor which receives the stream from the first conveyor and transports it along the second portion of the path), monitoring the mass or weight of material not later than in the second portion of the path (the monitoring step can be performed by resorting to a suitable measuring device, for example, a weighing device which can ascertain the mass of successive unit lengths of the stream in the first or second portion of the path), changing the volume of material leaving the first portion of the path when the monitored mass deviates from a predetermined value (for example, the changing step can include varying the speed of the first conveyor, and hence the speed of the stream in the first portion of the path, if the cross-sectional area of the stream in the first portion of the path is constant or nearly constant), generating first signals denoting the volume of material leaving the first portion of the path (this can be achieved by resorting to a tachometer generator which ascertains the speed of the prime mover means for the first conveyor), generating second signals denoting the mass of material leaving the second portion of the path (if the monitoring means is a weighing device which is adjacent to the second portion of the path, the means for generating second signals can include a potentiometer which ascertains the extent of pivotal movement of a pivotable arm or weighbeam forming part of the weighing device and being arranged to change its position in dependency on changes in the weight of successive unit lengths of the tobacco stream on the second conveyor), and utilizing the first and second signals for generation of third signals denoting the bulk weight of the material of the stream. At the present time, the utilizing step preferably comprises dividing the first signals with the corresponding second signals; the resulting quotients constitute the third signals and are indicative of or proportional to the bulk weight of the material of the stream.

As mentioned above, the step of conveying the stream along the first portion of the path can include maintaining the cross-sectional area of the stream at a substantially constant value. The step of changing the volume of material leaving the first portion of the path then includes varying the speed of the stream in the first portion of the path when the monitored mass in the second portion of the path deviates from the predetermined value. Also, the first signals then denote the speed of the stream in the first portion of the path.

The second portion of the path can discharge the stream at a constant speed. For example, the second portion can be defined by the trough of a vibratory conveyor which is vibrated by a constant-speed motor.

The monitoring step can be carried out upon the material which has already entered the second portion of the path. Alternatively, the monitoring step can be carried out during entry of particulate material into the second portion of the path. The method then further comprises the steps of monitoring the speed of material immediately prior to or during entry into the second portion of the path, generating fourth signals denoting the speed of successive unit lengths of the stream entering the second portion of the path (such fourth signals can be generated by a tachometer generator which is driven by a variable-speed prime mover for the second conveyor), generating fifth signals denoting the products of the second and fourth signals (i.e., the products of signals which respectively indicate the mass and the speed of successive unit lengths of the stream in the second portion of the path), and utilizing the fifth signals for regulation of the speed of material in the second portion of the path so that the products remain at least substantially unchanged. The utilizing step can include resorting to an amplifier for the prime mover which drives the second conveyor, and the amplifier varies the speed of the second conveyor in such a way that the products of second and fourth signals vary little or not at all.

In accordance with one presently preferred embodiment of the invention, the method further comprises the steps of generating first additional (fourth) signals denoting the speed of particulate material which leaves the second portion of the path, multiplying the second signals with the first additional signals to generate second additional (fifth) signals, utilizing the second additional signals to regulate the speed of advancement of material in the second portion of the path so that the characteristics (e.g., voltage) of second additional signals remain substantially unchanged, generating third additional (sixth) signals denoting the extent and duration of deviation of one of the second and first additional signals from a preselected value (this can be achieved by resorting to a suitable function generator circuit having two inputs which receive the second and first additional signals and an output for transmission of the aforementioned third additional signals), multiplying the third additional signals with the other of the second signals and first additional signals to generate fourth additional (seventh) signals, and utilizing the fourth additional signals to regulate the speed of material in the first portion of the path.

The second signals can denote the desired or actual mass of material leaving the second portion of the path.

The method can further comprise the steps of establishing and maintaining a substantially constant supply of particulate material upstream of the first portion of the path (for example, such supply can be established and maintained in an upright duct or an analogous container for tobacco leaves or the like) and feeding the material from the supply into the first portion of the path to form the aforementioned stream. The just discussed method can further comprise the steps of establishing and maintaining a second supply of material upstream of the first supply, transferring material from the second supply into the first supply at a variable rate, monitoring the volume of the first mentioned supply (e.g., by resorting to one or more level detectors installed in the aforementioned duct), and varying the rate of transfer of material from the second supply into the first supply when the monitored volume of the first supply is outside of a predetermined range.

The method can further comprise the steps of processing the material downstream of the second portion of the path, and utilizing the third signals to regulate the processing step. Thus, the processing step is carried out upon an equalized stream of particulate material. Such processing step can include subjecting particulate material of the equalized stream to the action of at least one current of gaseous fluid, and the step of utilizing the third signals then includes varying the characteristics of the current (e.g., the rate of flow of gaseous fluid) as a function of variation in the characteristics of third signals. As mentioned above, the third signals are indicative of (e.g., proportional to) the bulk weight of particulate material in the stream.

If desired, the method can further comprise the step of furnishing visual indications of the characteristics of third signals. This can be achieved by resorting to a suitable gauge whose pointer moves along a scale which is calibrated to indicate the bulk weight in kilograms per cubic meter. The gauge can be observed by attendants to ascertain whether or not the deviations of bulk weight and density from the optimum value are excessive.

The novel features which are considered as characteristic of the invention are set forth in particular in the appended claims. The improved apparatus itself, however, both as to its construction and its mode of operation, together with additional features and advantages thereof, will be best understood upon perusal of the following detailed description of certain specific embodiments with reference to the accompanying drawing.

BRIEF DESCRIPTION OF THE DRAWING

FIG. 1 is a schematic plan view of a production line including an apparatus which embodies the invention;

FIG. 2 is an enlarged fragmentary schematic elevational view of the apparatus;

FIG. 3 is a sectional view of a tobacco processing machine which forms part of the production line of FIG. 1 and receives a tobacco stream which is equalized by the apparatus of FIG. 2;

DESCRIPTION OF THE PREFERRED EMBODIMENTS

Figure 4:
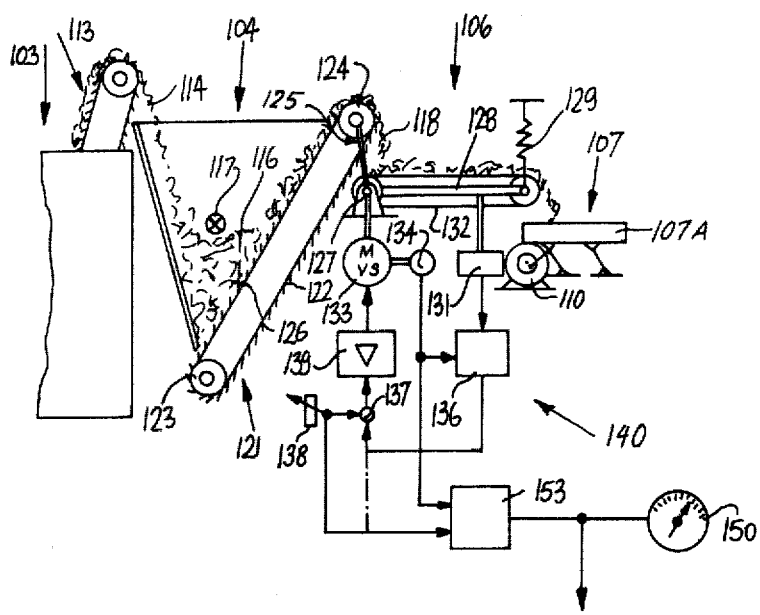
FIG. 4 illustrates a modified apparatus.

Referring first to FIG. 1, there is shown a complete production line for treatment of tobacco leaves. This line includes (as seen in the direction which is indicated by arrow 1) a tilting device 2 for evacuating the contents (namely, hogsheads, bales or similar accumulations of tobacco leaves) of carriages of the type known as WK (the device 2 can evacuate the contents of wagons or other types of vehicles which contain partially loosened tobacco leaves), a tobacco loosening and advancing device 3 of the type known as KTBL, a feeding unit 4 similar to that known as BZO, a signal generating weighing device 6 which resembles that known as DWB, a vibratory conveyor 7 of the type known as SR, a rotary tobacco conditioning drum 8 of the type known as WH, a band conveyor 9 of the type known as FBC, a vertical tobacco destalking device 11 which is similar to that known as VT 2500 S, and a device 12 for evacuation and transport of tobacco leaf laminae (this device is of the type known as 5 TSE). The aforementioned components (WK, KTBL, etc.) of the production line shown in FIG. 1 are manufactured and sold by the assignee of the present application.

FIG. 2 shows that the loosening and advancing device 3 comprises an endless carded conveyor 13 which delivers a stream of tobacco leaves 14 into a container or magazine 4A of the feeding unit 4. One side wall of the magazine 4A forms part of a conveyor 21 (first conveyor of the equalizing apparatus) including an endless belt 26 which is trained over pulleys 23 and 24. The carding (e.g., pins) of the belt 26 is shown at 22. The magazine 4A contains a substantially constant intermediate supply 16 of tobacco leaves 14. The supply 16 is monitored by a level detector system including one or more photocells 17 which form part of a two-point regulating system for the speed of the conveyor 13. This insures that the upper level of the intermediate supply 16 varies very little or not at all. The details of a regulating system which can be used to vary the speed of the conveyor 13 in dependency on changes of the upper level of a supply of tobacco leaves or the like are disclosed in the commonly owned U.S. Pat. No. 3,903,901 and in the corresponding commonly owned German Pat. No. 1,914,466 to both of which reference may be had, if necessary. A similar regulating system is shown in FIG. 4.

The upwardly sloping reach of the belt 26 of the conveyor 21 draws from the supply 16 a continuous unequalized tobacco stream 18 which is caused to travel around the upper pulley 24 and successive increments or unit lengths of which descend onto the upper reach of an endless belt conveyor 32 (second conveyor of the equalizing apparatus) forming part of the signal generating weighing device 6. The conveyor 32 is driven by a variable-speed prime mover 33 (preferably a DC-motor) and is supported by a substantially horizontal weighbeam or arm 28 of the weighing device 6. The arm 28 is pivotable about the horizontal axis of a fulcrum 27. The pulleys for the conveyor 32 are shown at 32A, 32B; the pulley 32A is driven by the prime mover 33 so that the upper reach of the conveyor 32 advances in a direction to the right, as viewed in FIG. 2. The stream 18 is converted into an equalized stream 18A as it descends onto the upper reach of the conveyor 32, and successive unit lengths of the equalized stream 18A (wherein the weight of each unit length is identical with or closely approximates a predetermined weight) are thereupon delivered into the trough 7A of the vibratory conveyor 7. That end portion of the arm 28 which is remote from the fulcrum 27 is biased upwardly by one or more helical springs 29 or other suitable biasing means (e.g., one or more weights suspended on cords and attached to the arm 28 in such a way that the right-hand end portion of the arm tends to move upwardly).

The left-hand pulley 32A for the conveyor 32 is coaxial with the fulcrum 27. The arm 28 supports the conveyor 32 and the equalized tobacco stream 18A in that portion of an elongated path for tobacco leaves which extends above the upper reach of the conveyor 32. The preceding portion of such path is defined by the conveyor 21 of the feeding unit 4, and the next-following portion of such path is defined by the trough 7A of the vibratory conveyor 7.

The arm 28 cooperates with a signal generating device 31 here shown as an adjustable potentiometer whose wiper (not specifically shown) is displaced in response to pivoting of the arm 28 about the axis of the fulcrum 27. Such pivoting takes palce under the action of gravity which is normally assisted by the weight of tobacco leaves 14 on the conveyor 28 or under the action of the biasing means 29. The means for transmitting motion from the arm 28 to the wiper of the potentiometer 31 includes a connecting rod 31A or the like. The potentiometer 31 transmits a series of signals which are indicative of the mass or weight of successive unit lengths of the tobacco stream 18A on the belt 32. Such signals are transmitted to one input of a multiplying (signal modifying) circuit 36 and to one input of an adding circuit 41.

The speed of the prime mover 33, and hence the speed of the conveyor 32, is monitored by a signal generating device 34 which is a tachometer generator and whose output is connected to a second input of the multiplying circuit 36 as well as to one input of a second multiplying circuit 46. The signals of the series of signals appearing at the output of the tachometer generator 34 denote the speed of corresponding unit lengths of the tobacco stream on the conveyor 32.

The multiplying circuit 36 may be of the type described on pages 1179 to 1190 of the publication entitled "Taschenbuch der Nachrichtenverarbeitung" by K. Steinbuch (published 1962 by Springer Verlag, Federal Republic Germany). The signal at the output of the circuit 36 is transmitted to one input of a signal comparing stage 37 another input of which receives a reference signal from a suitable source 38 (e.g., an adjustable potentiometer). The output of the stage 37 is connected with an operational amplifier 39 which controls the speed of the prime mover 33. The amplifier 39 regulates the speed of the prime mover 33 in such a way that the product of a first signal (from the potentiometer 31) denoting the mass or weight of a unit length of the tobacco stream on the conveyor 32 and a second signal (from the tachometer generator 34) denoting the speed of such unit length on the belt conveyor 32 is constant or nearly constant. The multiplying circuit 36, stage 37, potentiometer 38 and amplifier 39 together constitute a regulating means 40 for the weighing device 6.

The other input of the adding circuit 41 is connected with a source 42 (e.g., an adjustable potentiometer) of reference signals. The arrangement is such that the intensity of the signal at the output of the adding circuit 41 is zero if the intensity of signals at the two inputs of this circuit is identical. The output of the circuit 41 is connected with one input of a function generator 43. The intensity of signal at the output of the function generator 43 is dependent on the extent and duration of change of the input signal (this is the so-called PI-behavior of the function generator). As shown in FIG. 2, the function generator 43 may comprise a capacitor 43A which is connected in parallel with an operational amplifier 43B.

Another input of the function generator 43 can be connected with the output of the potentiometer 38 during the initial stage of operation of the apparatus. The connection comprises a threshold circuit 44 having a switch 44A which can be opened or closed in response to signals from the potentiometer 31. The potentiometer 38 charges the capacitor 43A of the function generator 43 when the potentiometer 31 closes the switch 44A.

The outputs of the function generator 43 and of the tachometer generator 34 are connected to the respective inputs of the multiplying circuit 46 whose output is connected to one input of a signal comparing stage 47. Another input of the stage 47 is connected to a signal generating device 48 here shown as a tachometer generator which monitors the speed of a variable-speed prime mover 19 (preferably a DC-motor) for the conveyor 21, and the output of the stage 47 is connected with an operational amplifier 49 for the motor 19. The amplifier 49 forms part of a control circuit 52 for the motor 19. The reference character 51 denotes a regulating unit which includes the function generator 43, the multiplying circuit 46, the signal comparing stage 47 and the tachometer generator 48. The regulating unit 51 adjusts the control unit 52 so as to insure that the ratio of speeds of the coveyors 21 and 32 (i.e., the ratio of speeds of the prime movers 19 and 33) and can be changed automatically as a function of the extent and duration of a change in the characteristics of signals which are transmitted by the signal generating device 31 and/or 34.

The amplifier 49 evaluates the signals from the function generator 43 (subsequent to modification of such signals by the multiplying circuit 46) and varies the speed of the conveyor 21 accordingly, i.e., in dependency on the extent and duration of deviation of signals which are transmitted by the function generator 43 from a given value.

The circuitry of FIG. 2 further comprises a dividing or quotient forming circuit 53 for signals which are transmitted by the potentiometer 38 and tachometer generator 48. Instead of being connected with the potentiometer 38, one input of the dividing circuit 52 can receive signals from the output of the multiplying circuit 36; this is shown in FIG. 2 by a phantom line. The output of the dividing circuit 53 is connected with one input of a signal comparing stage 79 (FIG. 3) by an analog time-delay unit 55. The stage 79 forms part of circuitry which controls the operation of the tobacco destalking device 11. The connection between the dividing circuit 53 and the time-delay unit 55 includes a gauge 50 which indicates the intensity or another characteristic of signals transmitted to the stage 79. The delay which is effected by the time-delay unit 55 corresponds to the interval of time which is required to transport a unit length of the equalized tobacco stream 18A from the conveyor 32 of the weighing device 6 into the tobacco destalking device 11.

The trough 7A of the conveyor 7 is vibrated by a discrete motor 10.

The destalking device 11 is of the upright type and comprises a destalking unit 54 which is installed in a housing 56 in such a way that these parts define a classifying chamber 57 wherein the ribs are segregated from tobacco leaf laminae. The chamber 57 surrounds the unit 54 and a portion thereof is disposed above this unit. The outlet 56A of the housing 56 discharges tobacco leaf laminae into the evacuating device 12.

The band conveyor 9 delivers whole tobacco leaves 14 to an inlet including a air lock 58 which feeds the leaves to the destalking unit 54 by way of a vertical pipe 59 in the housing 56. The leaves descend into the range of a distributor 62 which is driven by an upright rotor 61 for a set of knives 69 rotating in a stationary basket 63 which allows separated ribs and laminae to leave the destalking unit 54 and to enter the lower portion of the chamber 57 by moving radially of and away from the rotor 61. The distributor 62 is spacedly surrounded by a stationary funnel 64 on top of the basket 63.

The lower end of the chamber 57 is closed by a spiral-shaped bottom wall 67 which may consist of sheet metal and is agitated by a vibrator 66. Tobacco ribs which descend onto the upper side of the bottom wall 67 are caused to enter an air lock 68 for evacuation from the housing 56. The means for intercepting and collecting the separated ribs is not specifically shown in the drawing.

The means for transmitting torque to the rotor 61 for the knives 69 comprises an electric motor 71 and a suitable transmission 72 (e.g., a transmission including one or more V-belts). A pipe or conduit 73 serves as a means for supplying compressed gas (preferably air) for segregation of ribs from tobacco leaf laminae. The pipe 73 discharges air into the space below the basket 63, and such air enters the chamber 57 by flowing through a foraminous conical wall 54A of the unit 54. The inlet of the pipe 73 is connected to a suitable source 73A of compressed gaseous fluid.

The means for regulating or influencing the rate of airflow into the housing 56 comprises a butterfly valve 74 in the pipe 73. The position of this valve (and hence the rate of airflow into the housing 56) is adjustable by a servomotor 76 which is controlled by an amplifier 82. The latter receives signals from the output of the aforementioned signal comparing stage 79. As explained hereinabove, one input of the stage 79 receives signals from the dividing circuit 53 via time-delay unit 55. Another input of the stage 79 is connected to a source 81 (e.g., an adjustable potentiometer) of reference signals, and a third input of the stage 79 is connected to the output of a signal generator 78 which is driven by a propeller 77 in the pipe 73. When the rate of fluid flow in the pipe 73 changes, the RPM of the propeller 77 also changes and the intensity or another characteristic of the signal at the output of the generator 78 changes accordingly. The reference character 83 denotes a control circuit arrangement which includes the signal generator 78, stage 79, potentiometer 81 and amplifier 82. When necessary, the control circuit arrangement 83 changes the angular position of the valve 74.

The operation:

Successive increments or unit lengths of the unequalized stream 18 which is formed and transported lengthwise and away from the intermediate supply 16 by the upwardly sloping reach of the belt 26 of the conveyor 21 in the feeding unit 4 are advanced over the pulley 24 and descend onto the upper reach of the conveyor 32 close to the fulcrum 27. This insures that dynamic forces which develop as a result of impingement of successive increments of the stream 18 upon the upper reach of the conveyor 32 cannot adversely influence the weighing action of the device 6. In other words, the lever arm of an increment which descends onto the conveyor 32 is practically nil because the locus of impingement of successive increments of the stream 18 upon the conveyor 32 is close to the fulcrum 27. Successive increments of the stream 18A thereupon advance toward the pulley 32B whereby their influence upon the angular position of the arm 28 (against the opposition of the spring 29) increases. The right-hand end of the arm 28 moves up and down, depending on the weight of successive increments, and thereby causes the potentiometer 31 (via connecting rod 31A) to generate a series of signals each denoting the mass or weight of the corresponding increment. The length of the path portion along which the increments move in the course of the weighing operation is determined by the length of the upper reach of the conveyor 32 and by the locus of impingement of increments which are fed by the belt 26.

Successive signals of the series of signals generated by the potentiometer 31 are transmitted to the corresponding input of the multiplying circuit 36 which further receives a series of signals from the tachometer generator 34, such signals denoting the speed of transport of successive increments of the tobacco stream above the arm 28. The output of the multiplying circuit 36 transmits voltage signals to the corresponding input of the signal comparing stage 37. Such voltage signals are indicative of the products of successive first signals from the potentiometer 31 and of successive corresponding second signals from the tachometer generator 34. Each voltage signal is a function of the speed of transport of tobacco along the path portion which is defined by the conveyor 32 and of the mass or weight of the corresponding increment of the stream (i.e., of the extent to which such increment causes the arm 28 to pivot clockwise against the opposition of the spring 29).

The signal comparing stage 37 further receives reference signals from the potentiometer 38; such reference signals are indicative of the desired voltage at the output of the multiplying circuit 36. If the intensity of reference signals from 38 deviates from the intensity of voltage signals, the stage 37 transmits a signal to adjust the amplifier 39, i.e., to change the speed of the prime mover 33 for the conveyor 32. The amplifier 39 is adjusted in such a way that the product of the first and second signals (output signal of the circuit 36) remains constant or reassumes a desired value with a minimum of delay as soon as the stage 37 detects a deviation from the desired value (intensity of signal transmitted by the potentiometer 38).

For example, if the weight of successive increments of the stream on the conveyor 32 increases, the intensity of first signals (at the output of the potentiometer 31) also increases. The nature of signals which the stage 37 then transmits to the amplifier 39 is such that the speed of the prime mover 33 is reduced. Inversely, when the extent to which the arm 28 is pivoted clockwise (against the opposition of the spring 29) decreases, the weight of successive increments of the stream is below the predetermined weight. The speed of the prime mover 33 is then increased. If the condition of the stream on the conveyor 32 matches that which is selected by adjustment of the potentiometer 42, the signal at the left-hand input of the adding circuit 41 matches and cancels the reference signal from the potentiometer 42 (such signals have opposite signs), i.e., the intensity of signal at the output of the adding circuit 41 is zero. The output of the function generator 43 then transmits a signal of given intensity (voltage) to the corresponding input of the multiplying circuit 46. Such signal is multiplied by the signal from the tachometer generator 34 (i.e., it is modified by a signal which is a function of the speed of the conveyor 32), and the resulting signal is transmitted to the stage 47 to constitute a reference signal. The stage 47 further receives a signal from the tachometer generator 48; when the intensity of such signal deviates from that of the signal at the output of the multiplying circuit 46, the amplifier 49 for the prime mover 19 is adjusted to change the speed of the conveyor 21 in the feeding unit 4. It will be noted that the speed of the conveyor 21 is a function of the speed of the conveyor 32. The intensity of signal at the output of the function generator 43 is constant when the signal at the output of the circuit 41 is zero; under such circumstances, the speed of conveyor 21 is only a function of the speed of the conveyor 32.

If the weight of successive increments of the tobacco stream on the conveyor 32 increases, the output of the adding circuit 41 transmits a negative signal and such negative signal causes the function generator 43 to reduce the intensity of the signal at its output (owing to the aforementioned PI behavior of the function generator). Consequently, the intensity of the signal at the output of the multiplying circuit 46 also decreases whereby the voltage of electric current supplied to the prime mover 19 by the amplifier 49 decreases, i.e., the RPM of the prime mover 19 is reduced and the speed of the conveyor 21 decreases. The RPM of the prime mover 19 decreases until the weight of successive increments on the conveyor 32 also decreases to such an extent that the intensity of signal at the output of the adding circuit 41 is zero. Thus, the consistency of the stream on the conveyor 32 of the weighing device 6 then matches that which is selected by the setting of the potentiometer 42. Inversely, the speed of the prime mover 19 is increased when the weight of successive increments of the stream on the conveyor 32 is less than the desired (predetermined) weight.

When the production line is started, the magazine 4A is normally empty or contains less than the optimum quantity of tobacco leaves, i.e., the upper level of the intermediate supply 16 is likely to be below that level at which the illustrated photocell 17 transmits a signal denoting that the quantity of tobacco in the magazine 4A is at an optimum value. In the absence of any remedial action, the speed of the prime mover 19 would be increased to an extremely high value whenever the quantity of tobacco leaves on the conveyor 32 is zero or well below the average value. Therefore, the upper input of the function generator 43 is then connected with the potentiometer 38 via closed switch 44A of the threshold circuit 44. The potentiometer 38 connects the function generator 43 with a source of electrical energy so as to charge the capacitor 43A. This insures that the speed of the prime mover 19 is not overly increased while the weighing device 6 is about to receive tobacco leaves 14, i.e., during starting of the production line. When the leaves 14 reach the conveyor 32 of the weighing device 6, the arm 28 pivots clockwise, as viewed in FIG. 2, and causes the connecting rod 31A to adjust the potentiometer 31 which, in turn, transmits a signal to the threshold circuit 44 to open the switch 44A and to thereby disconnect the potentiometer 38 from the capacitor 43A. From thereon, the speed of the conveyor 21 is regulated in the aforedescribed manner, i.e., the ratio of the speeds of conveyors 21, 32 is changed as a function of the extent and duration of deviation of signals transmitted by the potentiometer 31 from a desired value, i.e., as a function of deviation of the weight of successive increments on the conveyor 32 from the predetermined weight.

Since the tobacco stream 18A is constant owing to appropriate adjustment of the conveyor 21 which delivers the unequalized stream 18 to the weighing device 6, the density multiplied by the volume and speed of successive unit lengths of the stream 18 equals the product of weight and density of successive unit lengths of the stream 18A, and such product is constant.

It is assumed that the height of the unequalized stream 18 on the conveyor belt 26 is constant or nearly constant. Therefore, the density of the stream 18 can be said to equal "A" multiplied by one and divided by the speed of the belt 26. "A" denotes a factor corresponding to the aforementioned constant. Such factor varies in response to changes in adjustment of the potentiometer 38, i.e., in dependency on the desired mass or weight of successive unit lengths of the stream 18A.

The signal at the output of the dividing circuit 53 is a function of the desired consistency of the stream 18A (see the potentiometer 38 which is connected with one input of the circuit 53) and of the velocity of the stream 18 (whose volume is assumed to be constant). Therefore, the quotient signal at the output of the dividing circuit 53 is independent of the volume of the stream 18A but is always proportional to the density and bulk weight of this stream.

The signal at the output of the dividing circuit 53 is delayed by the unit 55 so as to account for the interval of time which is needed to transport a unit length of the stream 18A from the discharge end of the conveyor 32 to the inlet (air lock 58 shown in FIG. 3) of the tobacco destalking device 11. Such signal then reaches the corresponding input of the signal comparing stage 79 to be compared with signals from the potentiometer 81 and signal generator 78.

The operation of the destalking device 11 of FIG. 3 is as follows:

The leaves 14 which are delivered by the conveyor 9 enter the housing 56 via air lock 58 and the pipe 59 to be spread out in the funnel 64 by the distributor 62 which is driven by the rotor 61. The leaves 14 then enter the basket 63 of the destalking unit 54 and are propelled outwardly by the knives 69 which cooperate with the adjacent stationary parts of the basket to separate the ribs from tobacco leaf laminae. The mixture of ribs and laminae enters the portion of the chamber 57 which surrounds the basket 63.

The current of air which is delivered by the pipe 73 enters the lowermost portion of the chamber 57 via foraminous wall 54A and entrains the laminae upwardly toward and into the outlet 56A for transport into the evacuating device 12. The ribs (which are heavier than laminae) descend onto the bottom wall 67 and slide therealong toward and into the air lock 68 which is located at the lowermost point of the chamber 57.

The angular position of the valve 74 is regulated in dependency on the intensity of reference signal furnished by the potentiometer 81. The intensity of this signal is selected in dependency on the specific weight of tobacco leaves 14 which are delivered into the magazine 4A to form the intermediate supply 16. The speed of the gaseous fluid in the pipe 73 is monitored by the propeller 77 and signal generator 78. The signals (voltage) at the output of the signal generator 78 are indicative of such speed; these signals are transmitted to the stage 79 together with delayed signals from the output of the dividing circuit 53 and with the reference signal from the potentiometer 81. The stage 79 transmits a signal to the amplifier 82 to change the angular position of the valve 74 whenever the sum of intensities of signals transmitted to the stage 79 deviates from zero. This insures that the classifying operation in the chamber 57 invariably results in segregation of a maximum percentage of tobacco leaf laminae from ribs.

An important advantage of the improved method and apparatus is that the formation of an equalized stream 18A facilitates and simplifies the regulation of operation of the destalking device 11 and/or one or more additional tobacco processing machines downstream of the weighing device 6. The treatment of leaves downstream of the conveyor 32 is more predictable if the device or devices which receive tobacco from the conveyor 32 or from one of more intermediate conveyors are supplied an equalized tobacco stream. The operation of the destalking device 11 and/or one or more additional processing machines downstream of the conveyor 32 can be simplified and improved still further if the equalizing apparatus of FIG. 2 ascertains the bulk weight (density) of the stream 18. Thus, the operation of the device 11 can be regulated with a high degree of accuracy if the signals which are transmitted to the stage 79 via time-delay unit 55 denotes or are indicative of the bulk weight of tobacco. Therefore, the quality of material which issues from the destalking device 11 is also improved, together with the quality of products which are manufactured by resorting to such material. As explained above, eventual variations in the density of material of the equalized stream 18 A can be ascertained as soon as they develop so that the operation of the device 11 can be adjusted accordingly, i.e., as soon as a stream portion of different density reaches the air lock 58. This invariably reduces the likelihood of malfunctioning of the device 11 and/or of machine or machines which receive tobacco leaf laminae and/or ribs from the device 11. Moreover, the quality of ultimate products (e.g., plain cigarettes or filter cigarettes) is more uniform than in the absence of determination of bulk weight and modification of operation of the next-following machine or machines when the bulk weight changes.

The volume of the stream 18 on the conveyor 21 of the feeding unit 4 could be varied in several ways, e.g., by changing the cross-sectional area of the stream 18 or by changing the speed of the stream 18 while its cross-sectional area remains constant. The latter solution is preferred at this time because it is simpler to maintain the cross-sectional area of the stream at a substantially constant value. If the speed of the conveyor 21 were constant, eventual variations in the height of the stream 18 would be indicative of changes in the volume of the stream in that portion of the elongated path for tobacco leaves which extends from the magazine 4A to the conveyor 32 of the weighing device 6.

The apparatus of FIG. 2 is assumed to draw from the magazine 4A a continuous stream 18 having a constant height (cross-sectional area). Therefore, the speed of the conveyor 21 is varied by the amplifier 49 and prime mover 19 when the mass of tobacco on the conveyor 32 of the weighing device 6 changes. The signals at the output of the dividing circuit 53 (such signals are used to change the speed of the conveyor 21) are obtained by processing the signals (from the tachometer generator 48) which are indicative of the volume of tobacco leaves advancing with the upwardly sloping carded portion of the belt 26 and signals (from the circuit 36 or potentiometer 38) which are indicative of the mass of tobacco leaves on the conveyor 32.

In accordance with the invention, the density ($\rho$) of tobacco leaves in the equalized stream 18A equals $$G \cdot v2 / V \cdot v1$$

wherein G is the weight of the stream 18A, V is the volume of the stream 18, v2 is the velocity of the conveyor 32 and v1 is the velocity of the conveyor 21. The values of G, v2 and G can be maintained at a constant value; therefore, the density ($\rho$) equals the quotient of a constant and v1 (velocity of the stream 18 on the carded belt 26 of the conveyor 21).

The mass of the stream can be ascertained after the leaves reach the conveyor 32. Alternatively, the mass can be ascertained during or shortly prior to transfer of leaves onto the conveyor 32. This mode of ascertaining the mass exhibits the advantage that the stream can be equalized with an even higher degree of accuracy, also as regards eventual short-lasting deviations of the mass from a desired value. This involves the use of the aforediscussed multiplying circuit 36, stage 37, potentiometer 38 and amplifier 39 to change the speed of the prime mover 33 in such a way that the intensity or another characteristic of the signal at the output of the circuit 36 (product of signals denoting the speed and weight of unit lengths of tobacco leaves on the conveyor 32) remains constant.

Regulation of the speed of the prime mover 19 for the conveyor 21 further contributes to accuracy of equalization of the stream 18. As explained above, such regulation is carried out in addition to regulation of the speed of the conveyor 32 by multiplying the signal from the tachometer generator 36 with the signal from the function generator 43, i.e., with a signal denoting the duration and extent of deviations of the signal from the potentiometer 31 from a given value. The product of these signals is transmitted to the stage 47 and serves to regulate the operation of the amplifier 49, i.e., to vary the speed of the prime mover 19.

The signals at the output of the dividing circuit 53 are indicative of the bulk weight (density) of the stream 18A. The gauge 50 constitutes but one form of means for facilitating immediate determination of the density of the stream 18A. The scale of this gauge can be suitably calibrated to indicate the bulk weight of tobacco leaves.

When the weight or mass of the stream on the conveyor 32 is substantially constant without any help on the part of suitable monitoring, signal generating and other means, the potentiometer 31 can be replaced with a source of signals denoting the actual mass of the stream on the conveyor 32. Also, the apparatus then need not have any means for generating signals which denote the mass of tobacco leaves in that portion of the path which is defined by the conveyor 32. All that is necessary is to provide a gauge or other suitable means for indicating the selected mass of leaves on the conveyor 32. However, in most instances, the production line of FIG. 1 is used to transport and process different types of tobacco and/or to transport tobacco leaves at different rates, depending on the desired output of the production line and on the desired type of ultimate products. Therefore, the mass of tobacco on the conveyor 32 is likely to change and, consequently, the apparatus is preferably provided with means (31 or 38) which indicates the actual or desired mass of the stream.

The circuit arrangement 83 of FIG. 3 insures that variations of the bulk weight (density) of the stream 18A cannot adversely influence the operation of the sifting or classifying means in the destalking device 11. Thus, the system 83 takes into account the bulk weight (signals from the output of the dividing circuit 53) to adjust the rate of flow of gaseous fluid in the conduit 73 accordingly.

The equalizing apparatus of FIG. 4 differs from the apparatus of FIG. 2 in that the discrete prime mover (19 in FIG. 2) for the conveyor of the feeding unit is omitted. All such parts of the apparatus of FIG. 4 which are identical with or clearly analogous to corresponding parts of the apparatus of FIG. 2 are denoted by similar reference characters plus 100. The conveyor 132 of the weighing device 106 is kinematically coupled to the conveyor 121 of the feeding unit 104 by a chain drive 125 or the like. By changing the sprocket wheels for the chain of the drive 125, the ratio of speed of the conveyor 121 to the speed of the conveyor 132 can be varied in a simple and reproducible way so as to be indicative or a function of average density of the tobacco stream. In this embodiment of the invention, the conveyors 121 and 132 together constitute a composite first conveyor of the equalizing apparatus. The second conveyor of this modified apparatus is the trough 107A of the vibratory conveyor 107. The trough 107A is agitated by the motor 110.

The inputs of the dividing circuit 153 are connected with the tachometer generator 134 and with the source 138 of reference signals. Alternatively, and as shown in FIG. 4 by phantom lines, the lower input of the dividing circuit 153 can be connected with the output of the multiplying circuit 136.

The mode of regulating the operation of the weighing device 106 and of the conveyor 121 (via chain drive 125) is analogous to that of regulating the operation of the weighing device 6 of FIG. 2. The regulating unit is shown at 140; this unit includes the multiplying circuit 136, the signal comparing stage 137, the source 138 of reference signals, and the amplifier 139.

Figure 5:
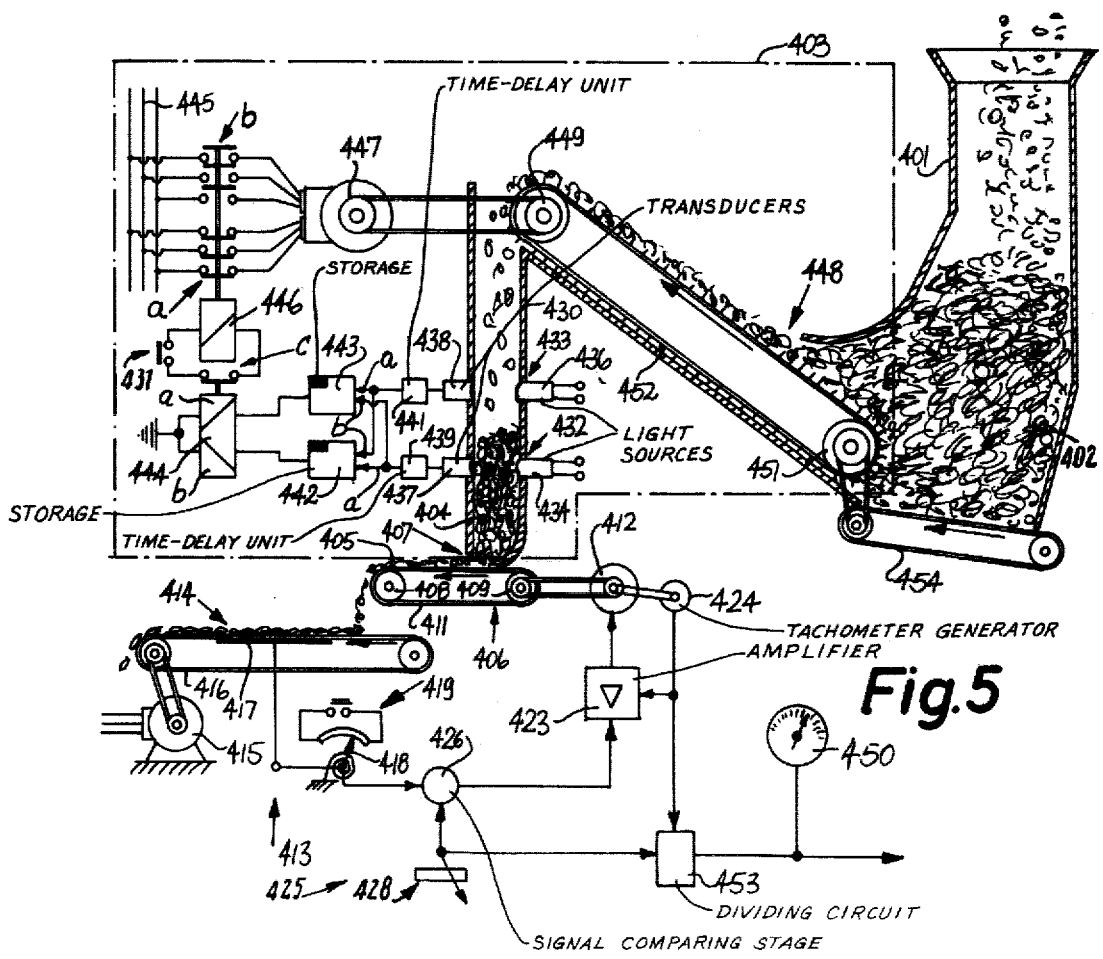
FIG. 5 is a partly elevational and partly vertical sectional view of a third apparatus.

The apparatus of FIG. 5 comprises a receptacle 401 for a large main supply 402 of flowable material (e.g., tobacco leaves). The leaves which are withdrawn from the receptacle 401 are delivered into a feeding unit 403 serving to establish and maintain a substantially constant intermediate supply 404 of tobacco leaves. The feeding unit 403 supplies tobacco leaves to a withdrawing device 406 which can form and advance a continuous and uniform layer or stream 405 of tobacco leaves onto the endless conveyor 414 of a weighing device 413. The conveyor 414 is driven by a motor 415.

The withdrawing device 406 is disposed below an opening 407 in the lowermost portion of an upright duct 430 forming part of the feeding unit 403 and serving to store the intermediate supply 404. The device 406 comprises one or more endless belts 411 which are trained over pulleys 408, 409. The pulley or pulleys 409 are driven by a variable-speed prime mover 412, e.g., a d-c motor. The conveyor including the belt or belts 411 and pulleys 408, 409 constitutes the first conveyor of the equalizing apparatus of FIG. 5.

The endless belt 416 of the conveyor 414 of the weighing device 413 is trained over pulleys and transports the layer or stream 405 (e.g., a carpet or fleece of tobacco leaves) above a weighbeam 417 which moves the wiper 418 of a potentiometer 419. The voltage at the wiper 418 of the potentiometer 419 (which constitutes the second signal generating means of the apparatus of FIG. 5) denotes the weight of tobacco leaves on the upper reach of the conveyor belt 416.

The wiper 418 is connected with a signal comparing stage 426 which further receives reference signals from an adjustable potentiometer 428 or another suitable source. The reference signal denotes the desired weight of tobacco leaves per unit length of the stream 405. The output of the stage 426 is connected with a regulator 423 for the speed of the prime mover 412. A suitable regulator is known as MINISEMI (produced by AEG, Federal Republic Germany). This regulator comprises a tachometer generator 424 which is shown outside of the box denoting the regulator 423 because it constitutes a (first) signal generating device connected with one input of a dividing circuit 453. The other input of the circuit 453 is connected with the potentiometer 428, and the output of the circuit 453 is connected with a gauge 450. Furthermore, the signal at the output of the dividing circuit 453 can be used to control the operation of a unit (e.g., the unit 11 of FIGS. 1 and 3) which processes the equalized tobacco stream, i.e., such signal can be used in the same way as the signal at the output of the dividing circuit 53 in FIG. 2.

The signal which is transmitted by the tachometer generator 424 is indicative of the speed of the belt or belts 411. The reference character 425 denotes a regulating unit for the prime mover 412; this regulating unit includes the signal comparing stage 426 and the potentiometer 428.

The feeding unit 403 includes a two-point regulating system 431 which controls the transfer of tobacco from the supply 402 in the receptacle 401 into the duct 430. The system 431 comprises two level detectors in the form of photocells 432 and 433 mounted on the duct 430 and serving to monitor the upper and lower levels of the intermediate supply 404. The photocells 432, 433 respectively comprise light sources 434, 436 and photoelectronic transducers 437, 438. The transducers 437, 438 are respectively connected in circuit with signal storing circuits 442, 443 via conventional time-delay devices 439, 441. The storing circuits 442, 443 have setting inputs a and erasing inputs b. The signals at the outputs of the circuits 442, 443 serve to energize the corresponding windings of a relay 444 which is in circuit with a second relay 446. The contacts a and b of the relay 446 can connect a variable-speed electric motor 447 with a source 445 of electrical energy. The motor 447 may constitute an asynchronous variable-polarity polyphase motor. When the contacts a are closed, the higher-pole-number winding of the motor 447 is connected to the source 445 so that the RPM of the motor is lower. The RPM of the motor 447 is higher when its lower-pole-number winding is connected to the source 445 via contacts b of the relay 446. The motor 447 forms part of the feeding unit 403 and serves to drive one of the pulleys 449, 451 for a carded belt conveyor 448 which transfers tobacco from the main supply 402. The carding of the conveyor 448 is shown at 452. The reference character 454 denotes a belt conveyor which constitutes a mobile bottom wall of the receptacle 401. One pulley for the conveyor 454 receives torque from the pulley 451.

The operation of the apparatus of FIG. 5 is as follows:

(a) Building of a substantially constant intermediate supply 404 of tobacco leaves or other particulate material in the duct 430 is regulated by the system 431 which causes the carded conveyor 448 to increase the rate of tobacco transfer from the main source of supply 402 when the upper level of material in the duct 430 sinks below the photocell 432, and to reduce the rate of tobacco delivery when the upper level of the supply 404 reaches the photocell 433. This insures that the volume of the supply 404 remains substantially constant, i.e., its upper level can fluctuate only between the levels of the photocells 432, 433. It is assumed that the upper level of the intermediate supply 404 is somewhere between the levels of the photocells 432 and 433 (as shown in FIG. 5). The output of the signal storing circuit 443 transmits a signal which energizes the respective winding a of the relay 444. The relay 444 maintains the contact c of the relay 446 in closed position. The contacts a of the relay 446 are also closed, i.e., the energy source 445 is connected with that winding of the motor 447 which causes the motor to drive the pulley 449 at a relatively low speed, namely, at a speed which is less than necessary to enable the conveyor 448 to deliver to the duct 430 tobacco leaves in such quantities as to compensate for the rate of withdrawal of tobacco leaves via opening 407. Therefore, the upper level of the intermediate supply 404 in the duct 430 sinks gradually so as to ultimately enable the light beam issuing from the source 434 to reach the transducer 437 of the lower photocell 432. The transducer 437 then transmits a signal to the erasing input b of the signal storing circuit 443 and to the setting input a of the signal storing circuit 442. Therefore, the signal at the output of the circuit 443 disappears and the output of the circuit 442 transmits a signal which energizes the corresponding winding b of the relay 444. The relay 444 then opens the contacts a and c and closes the contacts b of the relay 446. Thus, the energy source 445 is connected with the other winding of the motor 447. The latter then drives the conveyor 448 at a higher speed so that the rate of tobacco delivery to the duct 430 exceeds the rate of withdrawal via opening 407. Therefore, the upper level of the intermediate supply 404 begins to rise. The signal at the output of the signal storing circuit 442 remains intact after the rising intermediate supply 404 interrupts the light beam between the source 434 and transducer 437 of the lower photocell 432. When the supply 404 rises to the level of the photocell 433 and interrupts the light beam between the source 436 and transducer 438, the photocell 433 transmits a signal to the setting input a of the circuit 443 as well as to the erasing input b of the circuit 442. Thus, the signal at the output of the circuit 442 disappears and the circuit 443 causes the relays 444, 446 to reassume the conditions which are shown in the drawing. Therefore, the speed of the motor 447 is reduced and the upper level of the intermediate supply 404 begins to sink toward the level of the lower photocell 432. The signal at the output of the circuit 443 does not disappear when the uppermost stratum of the intermediate supply 404 in the duct 430 allows the light beam which issues from the source 436 to impinge upon the transducer 438 of the upper photocell 433. The speed of the motor 447 is increased again when the supply 404 allows the beam issuing from the source 434 to reach the transducer 437 of the lower photocell 432. The same procedure is repeated again and again, i.e., the upper level of the supply 404 fluctuates only between the levels of the photocells 432, 433. The time-delay devices 439 and 441 insure that short-lasting exposure of the lower transducer 437 to light issuing from the source 434 or short-lasting exposure of the upper transducer 438 to light issuing from the source 436 does not entail any changes in the speed of the motor 447. Such short-lasting interruptions of light beams issuing from the sources 434, 436 can be caused by tobacco leaves which descend in the duct 430 from the discharge end of the conveyor 448. The photocells 432 and 433 can be mounted sufficiently close to each other to insure that the fluctuations of intermediate supply 404 are relatively small, i.e., that they cannot adversely influence the uniformity of rate at which the belt 411 of the withdrawing device 406 removes tobacco leaves via opening 407. Excessive fluctuations of quantity of tobacco leaves in the duct 430 could cause undesirable fluctuations in the rate of withdrawal of leaves by the device 406.

(b) Removal of tobacco leaves from the intermediate supply 404 in the duct 430 is effected as follows: The belt 411 is driven by the prime mover 412, and its upper reach transports a continuous layer or carpet 405 of tobacco leaves toward and onto the upper reach of the belt 416 of the conveyor 414 in the weighing device 413. It has been found that the rate of delivery of tobacco leaves to the belt 416 is surprisingly constant as long as the height of the intermediate supply 404 varies within a relatively narrow range.

(c) Measurement or monitoring of the layer 405 by the weighing device 413: The weighbeam 417 cooperates with the wiper 418 so that the voltage signal which is furnished by the potentiometer 419 denotes the weight of successive unit lengths or increments of the layer 405. It can be said that the weighing device 413 transmits signals which denote the weight or mass of tobacco leaves per unit area of the upper reach of the conveyor belt 416. The signal at the wiper 418 is transmitted to the stage 426 to denote the actual weight of successive unit lengths or unit areas of the layer 405. Such signal is compared with the reference signal (desired weight) which is transmitted by the source 428. If the intensities or other characteristics of the two signals are different, the stage 426 transmits a signal to the regulator 423 which also receives a signal from the tachometer generator 424, i.e., a signal denoting the momentary speed of the motor 412 and belt 411 of the withdrawing device 406. When the intensities of the two signals are different, the regulator 423 changes the speed of the motor 412 and hence the rate of removal of tobacco via opening 407.

(d) The rate of tobacco withdrawal from the duct 430 is regulated by changing the speed of the motor 412 in dependency on the measurement of the layer 405 so as to maintain the quantity of tobacco in the layer 405 constant. As mentioned above, the regulator 423 (e.g., a suitabe amplifier) changes the speed of the motor 412 when the intensity of signal furnished by the stage 426 deviates from that of the signal which is transmitted by the tachometer generator 424. The adjustment of speed of the motor 412 is terminated when the rate of tobacco withdrawal from the duct 430 again matches the desired value (as denoted by the reference signal which is transmitted by the source 428). When the rate of withdrawal of tobacco from the duct 430 increases, the speed of the motor 412 and belt 411 is reduced, and vice versa.

If the material which is stored in the duct 430 consists of or includes tobacco shreds or like particles, the belt 411 can be (and preferably is) replaced with a toothed drum or carded belt which positively draws shreds from the opening 407 and cooperates with a rapidly driven picker roller serving to expel shreds from the spaces between the teeth or carding and to propel the expelled shreds onto the belt 416 of the conveyor 414 in the weighing device 413.

An important advantage of the apparatus of FIG. 5 is that the density of the material leaving the belt 416 can be ascertained with a very high degree of accuracy. This is due to the fact that the conveyor 411 draws tobacco leaves from a supply 404 whose volume is constant or nearly constant. This insures that the volume of the stream or layer 405 is also constant or nearly constant. It has been found that the buliding of a stream whose volume is constant or practically constant is much simpler and more reliable if the material forming such stream is withdrawn from a relatively small supply whose volume fluctuates very little or not at all. The system 431 monitors the volume of the supply 404 and causes the conveyor 448 to transfer tobacco from the main supply 402 at a different rate whenever the volume of the supply 404 rises above or drops below the range which is determined by the levels of the photocells 432 and 433.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of my contribution to the art and, therefore, such adaptations should and are intended to be comprehended within the meaning and range of equivalence of the appended claims.

I claim:

1. A method of continuously ascertaining the bulk weight of tobacco or other particulate material, comprising the steps of continuously conveying a stream of particulate material along a first and into and along a second portion of a predetermined path; monitoring the mass of material not later than in said second portion of said path; comparing the monitored mass with a predetermined value; changing the volume of material leaving said first portion of said path when the monitored mass deviates from said predetermined value; generating first signals denoting the volume of material leaving said first portion of said path; generating second signals denoting the mass of material leaving said second portion of said path; and utilizing said first and second signals for generation of third signals denoting the bulk weight of the material of said stream.

2. The method of claim 1, wherein said utilizing step comprises dividing said second signals with said first signals, the resulting quotients constituting said third signals.

3. The method of claim 1, wherein said step of conveying said stream along said first portion of said path includes maintaining the cross-sectional area of the stream at a substantially constant value and said step of changing the volume of material leaving said first portion of said path comprises varying the speed of the stream in said first portion when the monitored mass in said second portion of said path deviates from said predetermined value.

4. The method of claim 3, wherein said first signals denote the speed of the stream in said first portion of said path.

5. The method of claim 1, further comprising the step of discharging the material from said second portion of said path at a substantially constant speed.

6. The method of claim 1, wherein said monitoring step is carried out upon material which has already entered said second portion of said path.

7. The method of claim 1, wherein said monitoring step is carried out during entry of material into said second portion of said path and further comprising the steps of monitoring the speed of material immediately prior to or during entry of such material into said second portion of said path, generating fourth signals denoting the speed of successive unit lengths of the stream entering said second portion of said path, generating fifth signals denoting the products of said second and fourth signals, and utilizing said fifth signals for regulation of the speed of material in said second portion of said path so that said products remain at least substantially unchanged.

8. The method of claim 1, further comprising the steps of generating fourth signals denoting the speed of material leaving said second portion of said path, multiplying said second and fourth signals to generate fifth signals, utilizing said fifth signals to regulate the speed of advancement of material in said second portion of said path so that the characteristics of said fifth signals remain substantially unchanged, generating sixth signals denoting the extent and duration of deviation of one of said second and fourth signals from a preselected value, multiplying said sixth signals with the other of said second and fourth signals to generate seventh signals, and utilizing said seventh signals to regulate the speed of material in said first portion of said path.

9. The method of claim 1, wherein said second signals denote the desired or actual mass of material leaving said second portion of said path.

10. The method of claim 1, further comprising the steps of establishing and maintaining a substantially constant supply of material upstream of said first portion of said path and feeding material from said supply into said first portion of said path to form said stream.

11. The method of claim 10, further comprising the steps of establishing and maintaining a second supply of material upstream of said first mentioned supply, transferring material from said second supply into said first mentioned supply at a variable rate, monitoring the volume of said first mentioned supply, and varying said rate when the monitored volume is outside of a predetermined range.

12. The method of claim 1, further comprising the steps of processing the material downstream of said second portion of said path and utilizing said third signals to regulate said processing step.

13. The method of claim 12, wherein said processing step includes subjecting the material to the action of at least one current of gaseous fluid and said last mentioned utilizing step includes varying the characteristics of said current as a function of variations of the characteristics of said third signals.

14. The method of claim 1, wherein said third signals are proportional to the bulk weight of said material.

15. The method of claim 1, further comprising the step of furnishing visual indications of the characteristics of said third signals.

16. Apparatus for continuously ascertaining the bulk weight of tobacco or other particulate material, comprising a source of supply of particulate material; first conveyor means arranged to transport a tobacco stream from said source of supply along a first portion of a predetermined path; second conveyor means arranged to transport said stream from said first conveyor means along a second portion of said path; a measuring device adjacent to one of said conveyor means and including signal generating means for monitoring the mass of material in the respective portion of said path and for generating signals denoting the monitored mass; a source of reference signals denoting a predetermined value of the mass of material; means for comparing the signals denoting the monitored mass with said reference signals; means for changing the volume of material which is transported along said first portion of said path when the monitored mass deviates from said predetermined value; means for generating first signals denoting the volume of material leaving said first portion of said path; means for generating second signals denoting the mass of material leaving said second portion of said path; and means for correlating said first signals and said second signals to generate third signals denoting the bulk weight of the material of said stream.

17. Apparatus according to claim 16, wherein said correlating means comprises means for dividing said first signals with said second signals, the resulting quotients constituting said third signals.

18. Apparatus according to claim 16, wherein said stream has a substantially constant cross section in said first portion of said path and further comprising discrete first and second variable-speed prime mover means for said first and second conveyor means, respectively, said means for changing the volume of material which is transported along said first portion of said path including means for regulating the speed of said first prime mover means as a function of deviations of the characteristics of said second signals from a preselected value and said means for generating said first signals including means for monitoring the speed of said first conveyor means.

19. Apparatus according to claim 16, further comprising prime mover means for driving said second conveyor means at a substantially constant speed.

20. Apparatus according to claim 16, wherein said measuring device comprises a weighing device and said second conveyor means forms part of said weighing device.

21. Apparatus according to claim 16, wherein said measuring device includes a weighing device having an arm which is pivotable by the weight of successive unit lengths of the stream on said first conveyor means and said means for generating second signals includes means for monitoring the position of said arm, and further comprising means for generating fourth signals denoting the speed of the stream in said first portion of said path, means for multiplying said second and fourth signals to generate fifth signals, and means for regulating the speed of said first conveyor means so as to maintain said fifth signals at a substantially constant value.

22. Apparatus according to claim 16, wherein said measuring device includes a weighing device having an arm which is pivotable by successive unit lengths of the stream in said second portion of said path and said means for generating said second signals includes means for monitoring the position of said arm, and further comprising means for generating fourth signals denoting the speed of the material in said second portion of said path, means for multiplying said second and fourth signals to form fifth signals, means for varying the speed of said second conveyor means so as to maintain said fifth signals at a substantially constant value, means for generating sixth signals denoting the extent and duration of deviation of one of said second and fourth signals from a preselected value, means for multiplying said sixth signals with the other of said second and fourth signals to generate seventh signals, and means for varying the speed of said first conveyor means as a function of changes in the characteristics of said seventh signals.

23. Apparatus according to claim 16, wherein said means for generating second signals includes a source of reference signals denoting the desired mass of the stream in said second portion of said path.

24. Apparatus according to claim 16, wherein said means for generating second signals includes means for generating signals denoting the actual mass of unit lengths of the stream in one of said portions of said path.

25. Apparatus according to claim 16, wherein said source of supply includes a container for particulate material and further comprising means for maintaining the volume of particulate material and in said container within a predetermined range, said means for maintaining including a second source of particulate material, variable-speed third conveyor means for transporting material from said second source to said container, means for monitoring the level of material in said container, and means for changing the speed of said third conveyor means when the monitored level is outside of a preselected range of levels.

26. Apparatus according to claim 16, wherein said first conveyor means comprises an endless conveyor arranged to withdraw material from said source of supply.

27. Apparatus according to claim 26, wherein said source of supply includes a container having a lower portion and an opening in said lower portion, said endless conveyor being adjacent to said opening.

28. Apparatus according to claim 16, wherein said first conveyor means includes a carding and a material-withdrawing portion which is adjacent to said source of supply and slopes upwardly.

29. Apparatus according to claim 16, further comprising means for processing the material downstream of said second portion of said path.

30. Apparatus according to claim 29, further comprising means for regulating the operation of said processing means as a function of changes in the characteristics of said third signals.

31. Apparatus according to claim 30, wherein said processing means includes a pneumatic classifying device for the material of said stream and said classifying device includes means for conveying a current of gaseous fluid at a variable rate, said regulating means including means for varying said rate.

32. Apparatus according to claim 16, further comprising means for generating visible signals denoting the characteristics of said third signals.

* * * * *